(12) United States Patent
Saito et al.

(10) Patent No.: US 12,202,830 B2
(45) Date of Patent: Jan. 21, 2025

(54) METHOD FOR PRODUCING MORPHINAN DERIVATIVE

(71) Applicant: NIPPON CHEMIPHAR CO., LTD., Tokyo (JP)

(72) Inventors: Daisuke Saito, Misato (JP); Kohei Hayashida, Misato (JP)

(73) Assignee: NIPPON CHEMIPHAR CO., LTD., Tokyo (JP)

( * ) Notice: Subject to any disclaimer, the term of this patent is extended or adjusted under 35 U.S.C. 154(b) by 587 days.

(21) Appl. No.: 17/626,697

(22) PCT Filed: Jul. 17, 2020

(86) PCT No.: PCT/JP2020/027767
§ 371 (c)(1),
(2) Date: Jan. 12, 2022

(87) PCT Pub. No.: WO2021/015108
PCT Pub. Date: Jan. 28, 2021

(65) Prior Publication Data
US 2022/0267327 A1    Aug. 25, 2022

(30) Foreign Application Priority Data

Jul. 19, 2019    (JP) .................................. 2019-134051

(51) Int. Cl.
*C07D 471/08*    (2006.01)
(52) U.S. Cl.
CPC .................................. *C07D 471/08* (2013.01)
(58) Field of Classification Search
CPC .................................................... C07D 471/08
See application file for complete search history.

(56) References Cited

U.S. PATENT DOCUMENTS

| 5,504,208 A | 4/1996 | Sobotik et al. |
| 2014/0343015 A1 | 11/2014 | Nagase et al. |
| 2016/0122349 A1* | 5/2016 | Nagase .................... A61P 25/22 544/332 |
| 2018/0057493 A1 | 3/2018 | Nagase et al. |

FOREIGN PATENT DOCUMENTS

| JP | 2015-180605 | 10/2015 |
| WO | 2013/035833 | 3/2013 |
| WO | 2014/136305 | 9/2014 |
| WO | 2016/148232 | 9/2016 |

OTHER PUBLICATIONS

Peter G.M. Wuts et al.: "Reactivity Charts 8-10. Protection for the Amino Group" in "Greene's Protective Groups in Organic Synthesis", Jan. 1, 2014, John Wiley & Sons ProQuest Ebook Central, XP093006347, vol. 12, pp. 1298-1309.

Extended European Search Report issued in European Patent Application No. 20844453.9, Dec. 16, 2022.
Office Action issued in IN Patent Application No. 202247000907, Jul. 18, 2024, translation.
Sobi Asako et al., "Organosodium compounds for catalytic cross-coupling", Nature Catalysis, 2019, 2(4), pp. 297-303 Mar. 18, 2019.
Pirkle et al., "Journal of Organic Chemistry", 1965, pp. 1769-1773.
Li et al., "Bioorganic & Medicinal Chemistry Letters", 2009, pp. 4603-4606.
Zhang et al., "Journal of Medicinal Chemistry", 2007, pp. 2747-2751.
Li et al., "Chemical Biology & Drug Design", 2009, pp. 335-342.
Sawa et al., "Tetrahedron", 1968, pp. 6185-6196.
Selfridge et al., "Journal of Medicinal Chemistry", 2015, pp. 5038-5052.
Linders et al., "Recueil des Travaux Chimiques des pays-Bas", 1988, pp. 449-454.
Nagase et al., "J Org. Chem.", 2008, pp. 8093-8096.
Revesz et al., "Helvetica Chimica Acta", 1990, pp. 326-336.

(Continued)

*Primary Examiner* — Timothy R Rozof
(74) *Attorney, Agent, or Firm* — GREENBLUM & BERNSTEIN, P.L.C.

(57) ABSTRACT

Provided is, for example, a method for producing a morphinan derivative represented by General Formula (II), including the step of: allowing metal sodium and ethylenediamine to act on a morphinan derivative represented by General Formula (I) in presence of an auxiliary solvent.

[Chemical Formula 1]

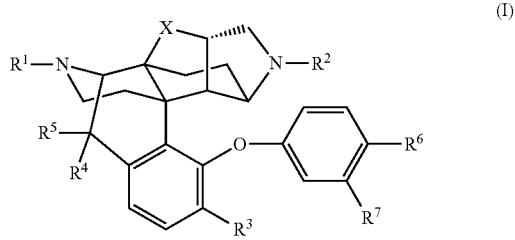

(I)

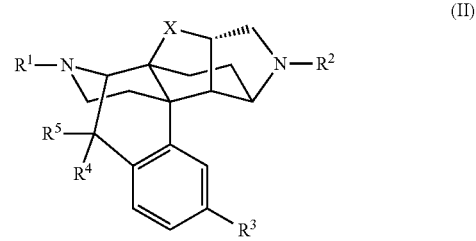

(II)

wherein $R^1$ represents a hydrogen atom, or a $C_{1-10}$ alkyl group, a $C_{3-6}$ cycloalkyl group, a $C_{2-6}$ alkenyl group, a $C_{6-10}$ aryl group, or a heteroaryl group optionally having a substituent, $R^2$ represents an amino protecting group, $R^3$ represents a methoxy group, $R^4$ and $R^5$ represent a hydrogen atom or a hydroxy group, $R^6$ and $R^7$ represent a hydrogen atom or an electron-donating group, wherein $R^6$ and $R^7$ are not simultaneously a hydrogen atom, and X represents O or $CH_2$.

38 Claims, No Drawings

(56) References Cited

OTHER PUBLICATIONS

Yoshikazu Watanabe et al., "Design and synthesis of novel d opioid receptor agonists with an azatricyclodecane skeleton for improving blood-brain barrier penetration, Bioorganic & Medicinal Chemistry Letters", 2017, pp. 3495-3498.
Kohei Hayashida et al., "Novel delta opioid receptor agonists with oxazatricyclodecane structure showing potent agonistic activities, Bioorganic & Medicinal Chemistry Letters", 2017, pp. 2742-2745.
Y. K. Sawa et al., "Elimination of the 4-hydroxyl group of the alkaloids related to morphine-IV", 1964, pp. 2255-2258.
International Search Report issued in International Application No. PCT/JP2020/027767, dated Aug. 18, 2020, along with an English translation thereof.

* cited by examiner

METHOD FOR PRODUCING MORPHINAN DERIVATIVE

TECHNICAL FIELD

The present invention relates to a method for producing a morphinan derivative, and a novel morphinan derivative that can be used as a starting material of the production method.

The present application claims priority based on Patent Application No. 2019-134051 filed in Japan on Jul. 19, 2019, the contents of which are incorporated herein by reference.

BACKGROUND ART

Three types of opioid receptors, μ, δ, and κ, are known, and morphine that exhibits strong affinity for the μ receptor has been used as an analgesic drug for a long time. Though the analgesic action of morphine is strong, morphine is known to cause adverse events such as dependence formation, respiratory depression, and constipation through μ receptors.

Meanwhile, the δ receptor also has an analgesic action, and the δ receptor agonist is known not to be involved in adverse events seen in morphine.

Thus, presumably, an agonist selective for the δ receptor can become an analgesic drug superior to morphine, and research on the creation thereof is actively conducted. However, there are still no δ receptor agonists approved as therapeutic or prophylactic agents.

Patent Literature 1 and Patent Literature 2 disclose morphinan derivatives having excellent δ receptor agonist activity and represented by the following formula.

[Chemical Formula 1]

The production of these derivatives needs multi-step synthesis, and thus the yield in one reaction and the purity of the target compound obtained by each reaction are desirably high.

For example, paragraph number [0025] of Patent Literature 1 discloses a technique in which a phenyl group is introduced into a 4-position phenol form (b-1) of a morphinan derivative by Ullmann reaction to form a compound (m), and an oxygen functional group at the 4-position is removed using sodium silica gel stage I which is commercially available sodium supported on silica gel and ethylenediamine to form a compound (n).

[Chemical Formula 2]

However, for example, there is a problem that the sodium supported on silica gel used in the above reaction is expensive, obtaining thereof in large quantities is difficult, and industrial use thereof is difficult.

Meanwhile, many examples in which metal sodium is used for a similar dephenoxylation reaction have been reported. For example, Non-Patent Literature 1 discloses a synthesis example of a compound 2 that is dephenoxylated by allowing metal sodium to act on a compound 1 having a 2,4-diaminophenyloxy group on a benzene ring of a morphinan skeleton in liquid ammonia.

[Chemical Formula 3]

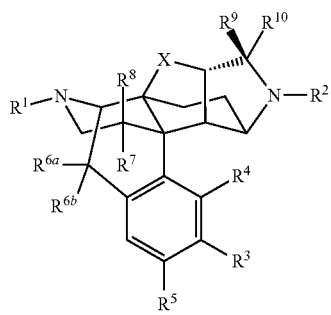

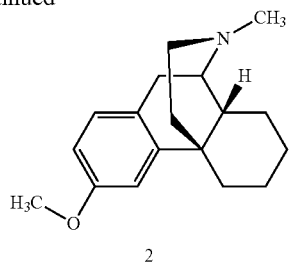

EXAMPLE 1 of Patent Literature 3 discloses an example of synthesis of 14β-hydroxy-3-methoxymorphinan (IV) by allowing metal sodium to act on 4-phenoxy-14β-hydroxy-3-methoxymorphinan (III) at −40° C. in liquid ammonia.

[Chemical Formula 4]

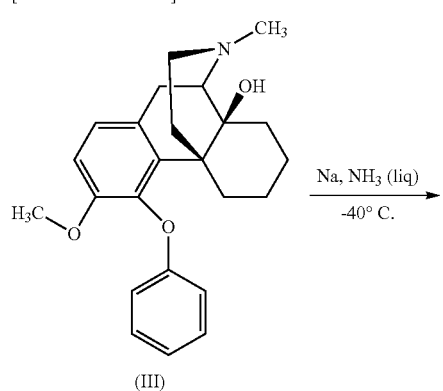

Non-Patent Literature 2 discloses a synthesis example of a compound 12 that is dephenoxylated by allowing metal sodium to act on a compound 11 having a phenoxy group at −78° C. to room temperature in liquid ammonia.

[Chemical Formula 5]

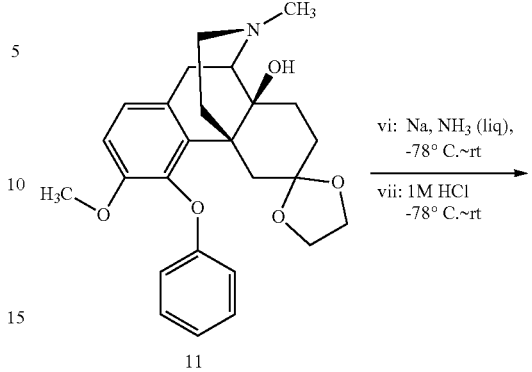

In addition, similar reactions have been also reported in Non-Patent Literatures 3 to 9.

CITATION LIST

Patent Literature

Patent Literature 1: WO 2013/035833
Patent Literature 2: WO 2016/148232
Patent Literature 3: U.S. Pat. No. 5,504,208

Non-Patent Literature

Non-Patent Literature 1: Journal of Organic Chemistry, 1965, 30 (6), 1769-1773
Non-Patent Literature 2: Bioorganic & Medicinal Chemistry Letters, 19 (16), 4603-4606; 2009
Non-Patent Literature 3: Chemical Biology & Drug Design, 74 (4), 335-342; 2009
Non-Patent Literature 4: Journal of Medicinal Chemistry, 50 (11), 2747-2751; 2007
Non-Patent Literature 5: Tetrahedron, 24 (20), 6185-96; 1968
Non-Patent Literature 6: Journal of Medicinal Chemistry, 58 (12), 5038-5052; 2015
Non-Patent Literature 7: Recueil des Travaux Chimiques des Pays-Bas, 107 (6), 449-54; 1988
Non-Patent Literature 8: Helvetica Chimica Acta, 73 (2), 326-36; 1990
Non-Patent Literature 9: J. Org. Chem. 2008, 73, 8093-8096

SUMMARY OF INVENTION

Technical Problem

The present inventors have found that in the production of a morphinan derivative (n) from a diaryl ether derivative (m) shown in paragraph number [0025] of Patent Literature 1, the morphinan derivative (n) being a dephenoxylated form thereof, there is a problem that the cleavage position of a bond between an oxygen atom and two aryl groups cannot be controlled, and cleavage occurs at an undesired position, so that in addition to the target dephenoxylated form (n), a compound (b-1), which is a raw material, is produced as a by-product, as shown in the lower figure. The compound (b-1) produced as a by-product at this time has a structure similar to that of the target dephenoxylated form (n), and is difficult to separate from the target product (n), and purification by chromatography is required. The present inventors have found that purification by chromatography is not preferable in an industrial production method and becomes a major problem.

Also, the present inventors performed a reaction similar to that in Patent Literature 1 using metal sodium pieces applicable to an industrial production method instead of sodium supported on silica gel having a problem in application to an industrial production method in the production of the compound (n) from the compound (m), and have found a problem that the reaction is not completed and a raw material remains even when a large excess of metal sodium pieces is used relative to the compound (m).

[Chemical Formula 6]

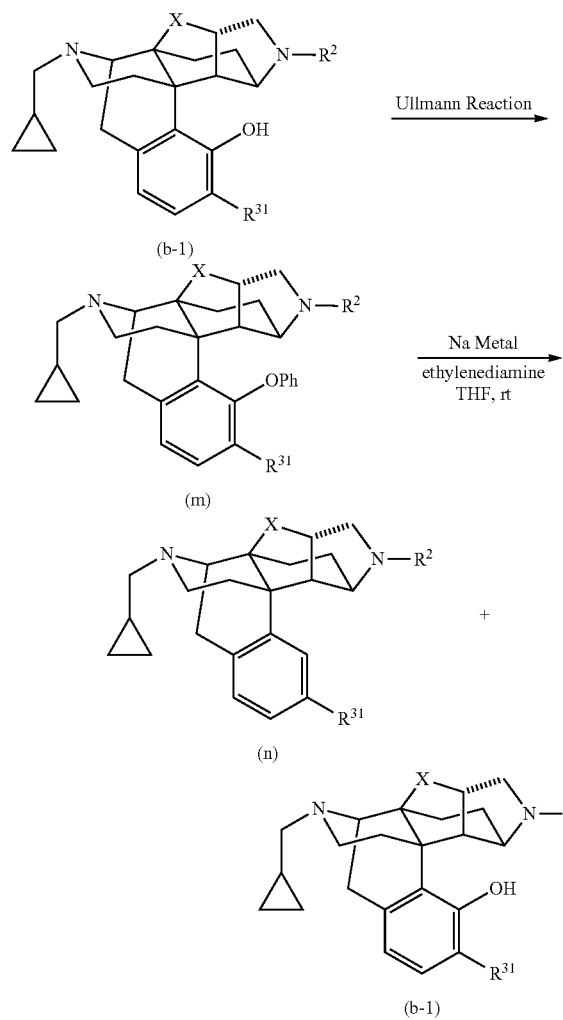

Thus, one object of the present invention is to provide a method for highly selectively producing a morphinan derivative (n) from a diaryl ether derivative (m) by suppressing production of a phenol form (b-1) as a by-product, the method being applicable to an industrial production method.

As a result of intensive studies on a production method of a morphinan derivative (n) described in paragraph number [0025] of Patent Literature 1, the present inventors have found that by using a compound in which a substituent is introduced at a specific position of a phenyl group introduced by an Ullmann reaction in the compound (b-1) as a starting material for a dearyloxylation reaction instead of the compound (m), high control of a cleavage position between oxygen and aryl groups becomes possible, and the target compound (n) is obtained with high selectivity. In addition, the present inventors have found that the target compound (n) can be obtained in a high yield by using a sodium dispersion which is also applicable to an industrial production method, thereby completing the present invention.

Solution to Problem

That is, the present invention relates to:
[1] a method for producing a morphinan derivative represented by General Formula (II) below:

[Chemical Formula 8]

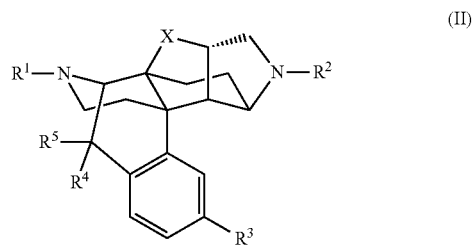

wherein $R^1$ represents a hydrogen atom, a $C_{1-10}$ alkyl group optionally having a substituent, a $C_{3-6}$ cycloalkyl group optionally having a substituent, a $C_{2-6}$ alkenyl group optionally having a substituent, a $C_{6-10}$ aryl group optionally having a substituent, or a heteroaryl group optionally having a substituent, $R^2$ represents an amino protecting group, $R^3$ represents a hydrogen atom, a halogen atom, or a $C_{1-10}$ alkoxy group optionally having a substituent, $R^4$ and $R^5$ are same or different and represent a hydrogen atom or a hydroxy group, and X represents O or $CH_2$, including the step of:

allowing metal sodium and ethylenediamine to act on a morphinan derivative represented by General Formula (I) below:

[Chemical Formula 7]

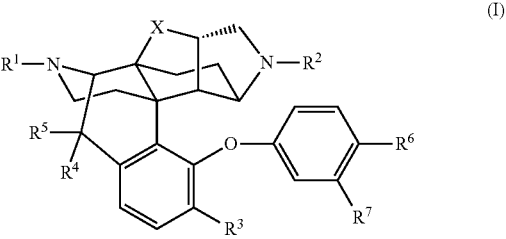

wherein R¹ to R⁵ and X have a meaning same as above,
R⁶ and R⁷ are same or different and represent a hydrogen atom or an electron-donating group,
wherein R⁶ and R⁷ are not simultaneously a hydrogen atom, and
in presence of an auxiliary solvent.

[2]
The present invention also relates to the method for producing a morphinan derivative according to [1] above, wherein R¹ is a hydrogen atom.

[3]
The present invention also relates to the method for producing a morphinan derivative according to [1] above, wherein R¹ is a $C_1$-10 alkyl group substituted with a $C_{3-6}$ cycloalkyl group optionally having a substituent.

[4]
The present invention also relates to the method for producing a morphinan derivative according to [1] or [3] above, wherein R¹ is a cyclopropylmethyl group.

[5]
The present invention also relates to the method for producing a morphinan derivative according to any one of [1] to [4] above, wherein R² is a benzyl group.

[6]
The present invention also relates to the method for producing a morphinan derivative according to any one of [1] to [5] above, wherein R³ is a $C_{1-10}$ alkoxy group.

[7]
The present invention also relates to the method for producing a morphinan derivative according to any one of [1] to [6] above, wherein R³ is a methoxy group.

[8]
The present invention also relates to the method for producing a morphinan derivative according to any one of [1] to [7] above, wherein R⁴ and R⁵ are a hydrogen atom.

[9]
The present invention also relates to the method for producing a morphinan derivative according to any one of [1] to [8] above, wherein R⁶ is a $C_1$-10 alkyl group, OR⁸ (R⁸ represents a hydrogen atom or a $C_{1-10}$ alkyl group optionally having a substituent), or NR⁹R¹⁰ (R⁹ and R¹⁰ are same or different and represent a hydrogen atom or a $C_{1-10}$ alkyl group optionally having a substituent).

[10]
The present invention also relates to the method for producing a morphinan derivative according to any one of [1] to [9] above, wherein R⁶ is a $C_{1-10}$ alkyl group optionally having a substituent.

[11]
The present invention also relates to the method for producing a morphinan derivative according to any one of [1] to [10] above, wherein R⁶ is a tert-butyl group.

[12]
The present invention also relates to the method for producing a morphinan derivative according to any one of [1] to [8] above, wherein R⁶ is a hydrogen atom.

[13]
The present invention also relates to the method for producing a morphinan derivative according to any one of [1] to [11] above, wherein R⁷ is a hydrogen atom.

[14]
The present invention also relates to the method for producing a morphinan derivative according to any one of [1] to [12] above, wherein R⁷ is a $C_{1-10}$ alkyl group optionally having a substituent, OR¹¹ (R¹¹ represents a hydrogen atom or a $C_{1-10}$ alkyl group optionally having a substituent), or NR¹²R¹³ (R¹² and R¹³ are same or different and represent a hydrogen atom or a $C_{1-10}$ alkyl group optionally having a substituent).

[15]
The present invention also relates to the method for producing a morphinan derivative according to any one of [1] to [12] and [14] above, wherein R⁷ is a $C_{1-10}$ alkoxy group optionally having a substituent.

[16]
The present invention also relates to the method for producing a morphinan derivative according to any one of [1] to [12], [14], and [15] above, wherein R' is a methoxy group.

[17]
The present invention also relates to the method for producing a morphinan derivative according to any one of [1] to [16] above, wherein the metal sodium is used in an amount of 1 to 10 equivalents relative to the morphinan derivative of the General Formula (I).

[18]
The present invention also relates to the method for producing a morphinan derivative according to any one of [1] to [17] above, wherein the metal sodium is a metal sodium dispersion.

[19]
The present invention also relates to the method for producing a morphinan derivative according to any one of [1] to [18] above, wherein the auxiliary solvent is an aromatic hydrocarbon solvent or an ether solvent.

[20]
The present invention also relates to the method for producing a morphinan derivative according to any one of [1] to [19] above, wherein a reaction temperature is −30° C. to 150° C.

[21]
The present invention also relates to the method for producing a morphinan derivative according to any one of [1] to [20] above, wherein a reaction temperature is 0° C. to 30° C.

[22]
The present invention also relates to a morphinan derivative represented by General Formula (I) below:

[Chemical Formula 9]

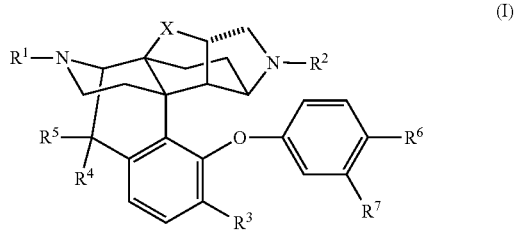

wherein R¹ represents a hydrogen atom, a $C_{1-10}$ alkyl group optionally having a substituent, a $C_{3-6}$ cycloalkyl group optionally having a substituent, a $C_{2-6}$ alkenyl group optionally having a substituent, a $C_{6-10}$ aryl group optionally having a substituent, or a heteroaryl group optionally having a substituent, R² represents an amino protecting group, R³ represents a hydrogen atom, a halogen atom, or a $C_{1-10}$ alkoxy group optionally having a substituent, R⁴ and R⁵ are same or different and represent a hydrogen atom or a hydroxy group, $R^6$ and $R^7$ are same or different and represent a hydrogen atom or an electron-donating group, wherein $R^6$ and $R^7$ are not simultaneously a hydrogen atom, and X represents O or $CH_2$.

[23]

The present invention also relates to the morphinan derivative according to [22] above, wherein $R^1$ is a hydrogen atom.

[24]

The present invention also relates to the morphinan derivative according to [22] above, wherein $R^1$ is a $C_{1-10}$ alkyl group substituted with a $C_{3-6}$ cycloalkyl group optionally having a substituent.

[25]

The present invention also relates to the morphinan derivative according to [22] or [24] above, wherein $R^1$ is a cyclopropylmethyl group.

[26]

The present invention, the morphinan derivative according to any one of [22] to [25] above, wherein $R^2$ is a benzyl group.

[27]

The present invention also relates to the morphinan derivative according to any one of [22] to [26] above, wherein $R^3$ is a $C_{1-10}$ alkoxy group.

[28]

The present invention also relates to the morphinan derivative according to any one of [22] to [27] above, wherein $R^3$ is a methoxy group.

[29]

The present invention also relates to the morphinan derivative according to any one of [22] to [28] above, wherein $R^4$ and $R^5$ are a hydrogen atom.

[30]

The present invention also relates to the morphinan derivative according to any one of [22] to [29] above, wherein $R^6$ is a $C_1$-10 alkyl group, $OR^8$ ($R^8$ represents a hydrogen atom or a $C_{1-10}$ alkyl group optionally having a substituent), or $NR^9R^{10}$ ($R^9$ and $R^{10}$ are same or different and represent a hydrogen atom or a $C_1$-10 alkyl group optionally having a substituent).

[31]

The present invention also relates to the morphinan derivative according to any one of [22] to [30] above, wherein $R^6$ is a $C_{1-10}$ alkyl group optionally having a substituent.

[32]

The present invention also relates to the morphinan derivative according to any one of [22] to [31] above, wherein $R^6$ is a tert-butyl group.

[33]

The present invention also relates to the morphinan derivative according to any one of [22] to [29] above, wherein $R^6$ is a hydrogen atom.

[34]

The present invention also relates to the morphinan derivative according to any one of [22] to [32] above, wherein $R^7$ is a hydrogen atom.

[35]

The present invention also relates to the morphinan derivative according to any one of [22] to [33] above, wherein $R^7$ is a $C_1$-10 alkyl group optionally having a substituent, $OR_{11}$ ($R^{11}$ represents a hydrogen atom or a $C_{1-10}$ alkyl group optionally having a substituent), or $NR^{12}R^{13}$ ($R^{12}$ and $R^{13}$ are same or different and represent a hydrogen atom or a $C_{1-10}$ alkyl group optionally having a substituent).

[36]

The present invention also relates to the morphinan derivative according to any one of [22] to [33] and [35] above, wherein $R^7$ is a $C_{1-10}$ alkoxy group optionally having a substituent.

[37]

The present invention also relates to the morphinan derivative according to any one of [22] to [33], [35], and [36] above, wherein $R^7$ is a methoxy group.

[38]

Further, the present invention relates to a morphinan derivative selected from (1S,3aR,5aS,6R,11bS,11cS)-3-benzyl-11-(4-(tert-butyl)phenoxy)-14-(cyclopropylmethyl)-10-methoxy-2,3,3a,4,5,6,7,11c-octahydro-1H-6,11b-(epiminoethano)-1,5a-methanonaphtho[1,2-e]indole, (1S,3aR,5aS,6R,11bS,11cS)-3-benzyl-14-(cyclopropylmethyl)-10-methoxy-11-(3-methoxyphenoxy)-2,3,3a,4,5,6,7,11c-octahydro-1H-6,11b-(epiminoethano)-1,5a-methanonaphtho[1,2-e]indole, and (1S,3aR,5aS,6R,11bS,11cS)-3-benzyl-14-(cyclopropylmethyl)-10-methoxy-11-(p-toluyloxy)-2,3,3a,4,5,6,7,11c-octahydro-1H-6,11b-(epiminoethano)-1,5a-methanonaphtho[1,2-e]indole.

Advantageous Effects of Invention

According to the present invention, a method for highly selectively producing a morphinan derivative (n) from a diaryl ether derivative (m) by suppressing production of a phenol form (b-1) as a by-product, the method being applicable to an industrial production method can be provided.

DESCRIPTION OF EMBODIMENTS

The present invention will be next described in more detail.

In the General Formula (I), examples of the $C_{1-10}$ alkyl group optionally having a substituent of $R^1$ include a $C_{1-10}$ alkyl group optionally having a substituent selected from a halogen atom, a hydroxy group, a $C_{1-10}$ alkoxy group, an amino group and the like; a $C_{1-10}$ alkyl group substituted with a $C_{3-6}$ cycloalkyl optionally having a substituent; an aralkyl group optionally having a substituent; and a heteroarylalkyl group optionally having a substituent.

Examples of the $C_{1-10}$ alkyl group of the $C_{1-10}$ alkyl group optionally having a substituent of $R^1$ include linear or branched $C_{1-10}$ alkyl groups such as a methyl group, an ethyl group, a propyl group, an isopropyl group, a butyl group, an iso-butyl group, a tert-butyl group, a pentyl group, and a hexyl group, preferably include a methyl group, an ethyl group, and a propyl group, and more preferably include a methyl group.

Examples of the $C_{1-10}$ alkyl group substituted with a $C_{3-6}$ cycloalkyl optionally having a substituent of $R^1$ include a methyl group and an ethyl group substituted with a $C_{3-6}$ cycloalkyl group such as a cyclopropyl group, a cyclobutyl group, a cyclopentyl group, and a cyclohexyl group, the cycloalkyl group optionally having a substituent selected from a halogen atom, a hydroxy group, a $C_{1-10}$ alkoxy group, an amino group and the like, preferably include a cyclopropylmethyl group, a cyclopropylethyl group, a cyclobutylmethyl group, and a cyclobutylethyl group, and more preferably include a cyclopropylmethyl group.

Examples of the aralkyl group optionally having a substituent of $R^1$ include an aralkyl group optionally having a substituent selected from a halogen atom, a hydroxy group, a $C_{1-10}$ alkoxy group, an amino group and the like, and having a carbon number of the aryl moiety of $C_{6-10}$ and a carbon number of the alkylene moiety of $C_{1-5}$, preferably include a methyl group and an ethyl group substituted with phenyl or naphthyl, and still more preferably include a methyl group substituted with phenyl (that is, a benzyl group).

Examples of the heteroarylalkyl group optionally having a substituent of $R^1$ include a heteroarylalkyl group in which the heteroaryl moiety optionally having a substituent selected from a halogen atom, a hydroxy group, a $C_{1-10}$ alkoxy group, an amino group and the like is a heteroaryl containing 1 to 4 heteroatoms that are same or different and selected from a nitrogen atom, an oxygen atom, and a sulfur atom, as ring-constituting atoms, and the alkyl moiety is a $C_{1-6}$ alkyl group such as a methyl group, an ethyl group, and a propyl group, and preferably include monocyclic heteroarylalkyl groups such as a (pyridine-2-yl)methyl group, a (pyridine-3-yl)methyl group, a (pyridine-4-yl)methyl group, a 2-(pyridine-2-yl)ethyl group, a (furan-2-yl)methyl group, a (furan-3-yl)methyl group, a (imidazole-2-yl)methyl group, a (imidazole-4-yl)methyl group, a (imidazole-5-yl)methyl group, a (thiazole-2-yl)methyl group, a (thiazole-4-yl)methyl group, a (thiazole-5-yl)methyl group, a (thiophene-2-yl)methyl group, and a 2-(thiophene-2-yl)ethyl group, and bicyclic heteroarylalkyl groups such as a (quinoline-3-yl)methyl group and a (indole-3-yl)methyl group.

Examples of the $C_{3-6}$ cycloalkyl group optionally having a substituent of $R^1$ in the General Formula (I) include a cyclopropyl group, a cyclobutyl group, a cyclopentyl group, and a cyclohexyl group optionally having a substituent selected from a halogen atom, a hydroxy group, a $C_{1-10}$ alkoxy group, an amino group and the like, and preferably include a cyclopropyl group.

Examples of the $C_{2-6}$ alkenyl group optionally having a substituent of $R^1$ in the General Formula (I) include alkenyl groups optionally having a substituent selected from a halogen atom, a hydroxy group, a $C_{1-10}$ alkoxy group, an amino group and the like, such as an allyl group, a vinyl group, a 1-propenyl group, a 2-butenyl group, a 3-butenyl group, a 2-pentenyl group, a 3-pentenyl group, a 4-pentenyl group, a 2-hexenyl group, a 3-hexenyl group, a 4-hexenyl group, and a 5-hexenyl group.

Examples of the $C_{6-10}$ aryl group optionally having a substituent of $R^1$ in the General Formula (I) include a phenyl group and a naphthyl group optionally having a substituent selected from a halogen atom, a hydroxy group, a $C_{1-10}$ alkoxy group, an amino group and the like, and a phenyl group is preferable.

Examples of the heteroaryl group optionally having a substituent of $R^1$ in the General Formula (I) include a heteroaryl group optionally having a substituent selected from a halogen atom, a hydroxy group, a $C_{1-10}$ alkoxy group, an amino group and the like and containing 1 to 4 heteroatoms that are same or different and selected from a nitrogen atom, an oxygen atom, and a sulfur atom, as ring-constituting atoms, and preferably include monocyclic heteroaryl groups such as a pyridyl group, a furyl group, an imidazolyl group, a pyrimidinyl group, a pyrazinyl group, and a thiazolyl group; and bicyclic heteroaryl groups such as a quinolyl group and an indolyl group.

Examples of the amino protecting group represented by $R^2$ include carbamate protecting groups such as a methoxycarbonyl group, an ethoxycarbonyl group, a tert-butoxycarbonyl group, a tert-amyloxycarbonyl group, a 2,2,2-trichloroethoxycarbonyl group, a benzyloxycarbonyl group, a p-chlorobenzyloxycarbonyl group, a p-methoxybenzylcarbonyl group, a p-nitrobenzyloxycarbonyl group, a p-phenylazobenzyloxycarbonyl group, a p-methoxyphenylazobenzyloxycarbonyl group, a 3,5-dimethoxybenzyloxycarbonyl group, a 3,4,5-trimethoxybenzyloxycarbonyl group, a p-biphenylisopropyloxycarbonyl group, a diisopropylmethyloxycarbonyl group, a 2-(trimethylsilyl)ethoxycarbonyl group, and a 9-fluorenylmethyloxycarbonyl group; sulfonamide protecting groups such as a p-toluenesulfonyl group and a 2-nitrobenzenesulfonyl group; acyl protecting groups such as an acetyl group and a trifluoroacetyl group; imide protecting groups such as a phthaloyl group; and $C_{7-19}$ aralkyl groups such as a benzyl group, a trityl group, and a naphthylmethyl group, preferably include a $C_{7-19}$ aralkyl group, and more preferably include a benzyl group.

Examples of the $C_{1-10}$ alkoxy group optionally having a substituent of $R^3$ include linear or branched $C_{1-10}$ alkoxy groups optionally having a substituent selected from a halogen atom, a hydroxy group, a $C_{1-10}$ alkoxy group, an amino group and the like, such as a methoxy group, an ethoxy group, a propoxy group, an iso-propoxy group, a butoxy group, an iso-butoxy group, a tert-butoxy group, a pentyloxy group, and a hexyloxy group, preferably include a methoxy group, an ethoxy group, and a propoxy group, and more preferably include a methoxy group.

Examples of the electron-donating group represented by $R^6$ include a $C_{1-10}$ alkyl group optionally having a substituent selected from a halogen atom, a hydroxy group, a $C_{1-10}$ alkoxy group, an amino group and the like, $OR^8$ ($R^8$ represents a hydrogen atom or a $C_{1-10}$ alkyl group optionally having a substituent), and $NR^9R^{10}$ wherein $R^9$ and $R^{10}$ are same or different and represent a hydrogen atom or a $C_{1-10}$ alkyl group optionally having a substituent.

Examples of the $C_{1-10}$ alkyl group optionally having a substituent of $R^8$ include linear or branched $C_{1-10}$ alkyl groups such as a methyl group, an ethyl group, a propyl group, an isopropyl group, a butyl group, an iso-butyl group, a tert-butyl group, a pentyl group, and a hexyl group, and preferably include a tert-butyl group.

Examples of $R^9$ and $R^{10}$ include an amino group, a methylamino group, a dimethylamino group, an ethylamino group, a diethylamino group, and a propylamino group.

$R^6$ is preferably a $C_{1-10}$ alkyl group, and examples thereof more preferably include a tert-butyl group.

Examples of the electron-donating group represented by $R^7$ include a $C_{1-10}$ alkyl group optionally having a substituent selected from a halogen atom, a hydroxy group, a $C_{1-10}$ alkoxy group, an amino group and the like, $OR_{11}$ ($R^{11}$ represents a hydrogen atom or a $C_{1-10}$ alkyl group optionally having a substituent), and $NR^{12}R^{13}$ ($R^{12}$ and $R^{13}$ are same or different and represent a hydrogen atom or a $C_{1-10}$ alkyl group optionally having a substituent).

Examples of the $C_{1-10}$ alkyl group optionally having a substituent of $R^{11}$ include the same as those of the $C_{1-10}$ alkyl group optionally having a substituent of $R^8$, and examples of $R^{12}$ and $R^{13}$ include the same as those of $R^9$ and $R^{10}$.

Examples of X include an oxygen atom and $CH_2$, and $CH_2$ is preferable.

In the present specification, examples of the halogen atom include a fluorine atom, a chlorine atom, a bromine atom, and an iodine atom, preferably include a fluorine atom and a chlorine atom, and more preferably include a fluorine atom.

In the present specification, examples of the $C_{1-10}$ alkoxy group include linear or branched $C_{1-10}$ alkoxy groups such as a methoxy group, an ethoxy group, a propoxy group, an iso-propoxy group, a butoxy group, an iso-butoxy group, a tert-butoxy group, a pentyloxy group, and a hexyloxy group, preferably include a methoxy group, an ethoxy group, and a propoxy group, and more preferably include a methoxy group.

In the present specification, examples of the amino group include $NR^dR^e$ wherein $R^d$ and $R^e$ are same or different and examples thereof include a hydrogen atom and a $C_{1-10}$ alkyl group optionally having a substituent, and examples of the amino group preferably include an amino group, a dimethylamino group, and a diethylamino group.

Preferable combinations of these substituents include a case where $R^1$ is a $C_{1-10}$ alkyl group optionally having a substituent or a $C_{1-10}$ alkyl group substituted with a $C_{3-6}$ cycloalkyl optionally having a substituent;

$R^2$ is an amino protecting group;

$R^3$ is a methoxy group;

$R^4$ and $R^5$ are a hydrogen atom;

$R^6$ is a hydrogen atom or a $C_{1-10}$ alkyl group;

$R^7$ is a hydrogen atom or a methoxy group;

provided that one of $R^6$ and $R^7$ is a hydrogen atom, and the other is other than a hydrogen atom; and X is $CH_2$.

The compound represented by the General Formula (I) can be produced by a known method, for example, the method described in Patent Literature 1.

The production of the morphinan derivative represented by General Formula (II) can be performed by allowing metal sodium to act on the compound of the General Formula (I) in presence of ethylenediamine.

[Chemical Formula 10]

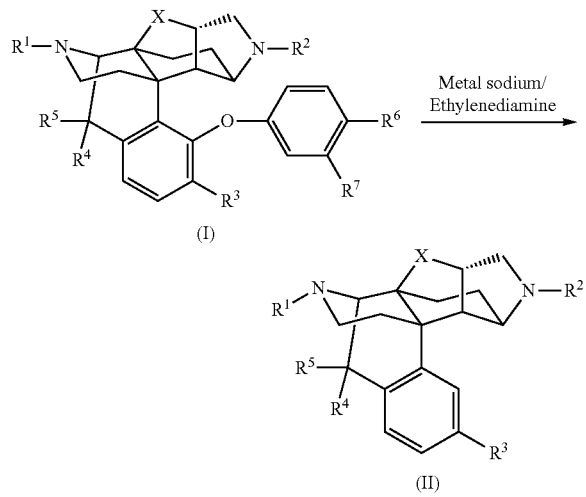

As the sodium reagent used in the above reaction, commercially available sodium reagents such as metal sodium and a metal sodium dispersion can be used, and a metal sodium dispersion is preferable.

In the present specification, the metal sodium dispersion refers to one obtained by dissolving sodium in an inert solvent having a boiling point of 100° C. or higher, and gradually cooling the solution while strongly stirring it to solidify the sodium. Examples of the particle size of the metal sodium dispersion used include 1 to 100 μm, preferably include 1 to 75 μm, more preferably include 1 to 50 μm, and still more preferably include 1 to 25 μm.

The amount of the sodium reagent used in the reaction is 1 to 50 equivalents, preferably 1 to 30 equivalents, more preferably 1 to 20 equivalents, still more preferably 1 to 10 equivalents, preferably 2 to 10 equivalents, and preferably 5 to 10 equivalents relative to the raw material.

Though other primary amines (for example, ethylamine, propylamine and the like) can be used instead of the ethylenediamine used in the above reaction, ethylenediamine is preferably used.

The amount of ethylenediamine or other primary amines used can be 1 to 100 mol, preferably 1 to 50 mol, more preferably 1 to 30 mol, still more preferably 1 to 20 mol, and more preferably 1.5 to 20 mol, relative to 1 mol of the sodium reagent.

Examples of the auxiliary solvent used in the above reaction include an aromatic hydrocarbon solvent and an ether solvent, examples of the aromatic hydrocarbon solvent include benzene, toluene, and xylene, and preferably include toluene, and examples of the ether solvent include tetrahydrofuran and 1,4-dioxane, and preferably include tetrahydrofuran.

Among these solvents, preferable examples include tetrahydrofuran.

For the amount of the auxiliary solvent used, though the amount of an organic solvent used is not particularly limited, it is preferably in a range of 1 to 50 parts by mass, and preferably in a range of 1 to 20 parts by mass relative to 1 part by mass of the morphinan derivative represented by the General Formula (I). These organic solvents are preferably used after being purified by a known method such as distillation.

The above reaction is preferably performed under an inert gas such as nitrogen or argon, the reaction temperature can be in the range of −30 to 150° C., preferably in the range of −10 to 120° C., and more preferably in the range of −5 to 115° C., and the target product can be obtained by reaction of 1 to 16 hours.

The morphinan derivative represented by General Formula (II) produced by the above method can be isolated and/or purified by applying a method known per se, for example, solvent extraction, concentration, crystallization, precipitation, filtration, chromatography, or the like. When the production method of the present invention is applied as an industrial production method, chromatography is preferably not used as a purification method from the viewpoint of production efficiency.

Thus, one embodiment of the present invention is the production method, including at least one step selected from solvent extraction, concentration, crystallization, precipitation, and filtration as the isolation and/or purification step of the morphinan derivative represented by General Formula (II), and not including the step of chromatography.

By applying the isolation and/or purification step, the morphinan derivative represented by General Formula (II) can be obtained, for example, with a purity of 75% or more, preferably with a purity of 80% or more, more preferably with a purity of 90% or more, still more preferably with a purity of 94% or more, and with a yield of 75% or more, preferably with a yield of 80% or more, more preferably with a yield of 85% or more, still more preferably with a yield of 90% or more, particularly preferably with a yield of 95% or more. At this time, the content of the phenol form (b-1) as a by-product in the target product can be 5% by mass or less, preferably 3% by mass or less, more preferably 1% by mass or less, and still more preferably 0% by mass (that is, the phenol form (b-1) is not contained), relative to the mass of the target product.

EXAMPLES

Hereinafter, the present invention will be described in more detail with reference to Examples, Reference Examples, Comparative Examples, and Test Examples, but the present invention is not limited thereto. For the naming of the compounds of Examples, the compounds of Reference Examples, and the compounds of Comparative Examples, the structural formulas drawn using ChemDraw ver. 15 manufactured by CambridgeSoft were converted into English names by a naming algorithm equipped in the same software, and then translated into Japanese.

1. Production of Starting Material: Diaryl Ether Derivative

A production example of a diphenyl ether derivative by Ullmann coupling of bromobenzene with (1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole-11-ol will be shown.

Reference Example 1

Synthesis of (1S,3aR,5aS,6R,11bS,11cS)-3-benzyl-14-(cyclopropylmethyl)-10-methoxy-11-phenoxy-2,3,3a,4,5,6,7,11c-octahydro-1H-6,11b-(epiminoethano)-1,5a-methanonaphtho[1,2-e]indole

[Chemical Formula 11]

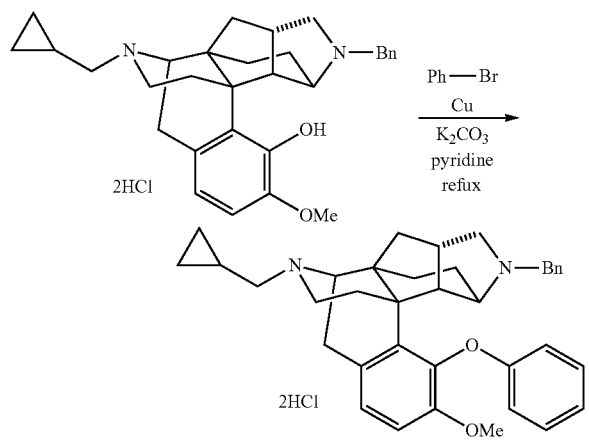

In a 300 mL round bottom flask, under a nitrogen atmosphere, (1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole-11-ol dihydrochloride (5 g, 1 equivalent) was dissolved in pyridine (50 mL). Potassium carbonate (3.8 g, 6 equivalents), bromobenzene (4.8 mL, 5 equivalents), and copper powder (0.6 g, 1 equivalent) were added to the obtained solution, and the mixture was heated and refluxed while being vigorously stirred. After 16 hours, the reaction was analyzed by mass spectrometry (MS) and thin layer chromatography, and the disappearance of the raw material was confirmed.

After cooling the reaction mixture to room temperature, the reaction mixture was filtered through a celite pad to remove insolubles. The pad was washed with ethyl acetate (50 mL) and methanol (50 mL), and 6% aqueous ammonia (50 mL) was added to the combined filtrate and washings. The organic layer and the aqueous layer were separated with a separating funnel, and the organic layer was fractionated. Further, the aqueous layer was extracted with ethyl acetate (50 mL×2 times). The combined organic layers were dried over anhydrous sodium sulfate, the anhydrous sodium sulfate was filtered off, and then the combined organic layers were concentrated under reduced pressure to obtain a title compound crude product.

The obtained crude product was dissolved in a 1:1 mixture (100 mL) of n-heptane and ethyl acetate, the solution was filtered through a short column packed with silica gel (35 g) using the same mixed solvent as an elution solvent, and the obtained filtrate was concentrated under reduced pressure to obtain the title compound (free form).

The obtained free form was dissolved in a 1:4 mixed liquid (50 mL) of n-heptane and ethyl acetate, and then a 4 N hydrogen chloride/ethyl acetate solution (5 mL) was slowly added at 0 to 5° C. with stirring to obtain a suspension.

The resulting solid was collected by filtration to obtain a hydrochloride of the title compound (5 g).

The obtained hydrochloride of the title compound was desalted with a 4 N aqueous sodium hydroxide solution (20 mL) to obtain the title compound (4.4 g, yield: 88%).

$^1$H-NMR (400 MHz, CDCl$_3$): δ7.10-7.35 (m, 7H), 6.90-7.05 (m, 2H), 6.70-6.85 (m, 3H), 6.72 (d, 1H, J=13 Hz), 3.68 (s, 3H), 3.58 (d, 1H, J=13 Hz), 2.90-3.25 (m, 6H), 2.60-2.75 (m, 3H), 2.45 (dd, 1H, J=5, 12 Hz), 2.29 (d, 2H, J=6 Hz), 1.99 (dt, 1H, J=3, 13 Hz), 1.50-1.80 (m, 3H), 1.10-1.25 (m, 1H), 1.00-1.10 (m, 2H), 0.70-0.85 (m, 2H), 0.40-0.55 (m, 2H), 0.00-0.15 (m, 2H).

A production example of a diaryl ether derivative by Ullmann coupling of other haloaryls with (1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole-11-ol will be shown below.

[Chemical Formula 12]

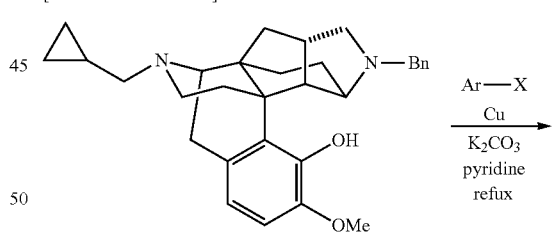

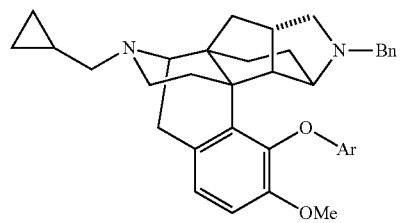

Example 1

Synthesis of (1S,3aR,5aS,6R,11bS,11cS)-3-benzyl-11-(4-(tert-butyl)phenoxy)-14-(cyclopropylmethyl)-10-methoxy-2,3,3a,4,5,6,7,11c-octahydro-1H-6,11b-(epiminoethano)-1,5a-methanonaphtho[1,2-e]indole

[Chemical Formula 13]

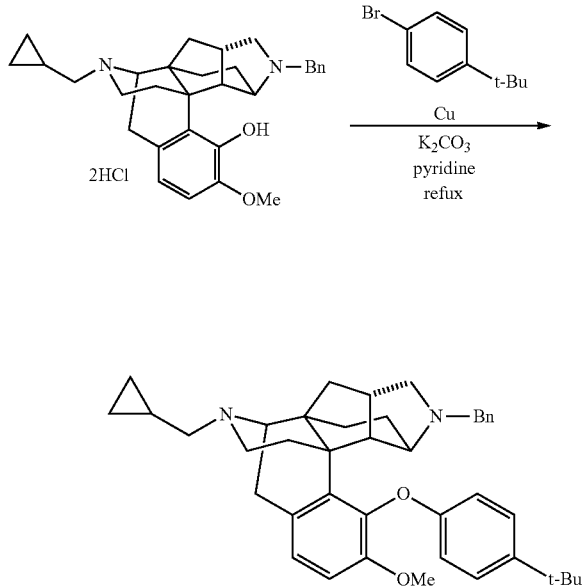

In a 2000 mL round bottom flask, under a nitrogen atmosphere, (1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole-11-ol dihydrochloride (30 g, 1 equivalent) was dissolved in pyridine (300 mL). Potassium carbonate (22.9 g, 3 equivalents), 4-tert-butylbromobenzene (47 mL, 5 equivalents), and copper powder (3.5 g, 1 equivalent) were added to the obtained solution, and the mixture was heated and refluxed while being vigorously stirred. After 16 hours, the reaction was analyzed by MS and thin layer chromatography to confirm that a small amount of the raw material remains. The temperature of the reaction liquid was once returned to room temperature, potassium carbonate (22.9 g, 3 equivalents), 4-tert-butylbromobenzene (47 mL, 5 equivalents), copper powder (3.5 g, 1 equivalent), and pyridine (300 mL) were added to the reaction liquid, and the mixture was heated and refluxed again while being vigorously stirred. After 24 hours, the reaction was analyzed by MS and thin layer chromatography, and complete disappearance of the raw material was confirmed.

After cooling the reaction mixture to room temperature, the reaction mixture was filtered through a celite pad to remove insolubles. The pad was washed with ethyl acetate (300 mL) and methanol (100 mL), and 6% aqueous ammonia (300 mL) was added to the combined filtrate and washings. The organic layer and the aqueous layer were separated with a separating funnel, and the aqueous layer was extracted with ethyl acetate (300 mL×2 times). The combined organic layers were dried over anhydrous sodium sulfate, the anhydrous sodium sulfate was filtered off, and then the combined organic layers were concentrated under reduced pressure to obtain a title compound crude product.

The obtained crude product was dissolved in a 1:1 mixture (300 mL) of n-heptane and ethyl acetate, the solution was filtered through a short column packed with silica gel (210 g) using the same mixed solvent as an elution solvent (2100 mL), and the obtained filtrate was concentrated under reduced pressure to obtain the title compound (free form). The obtained free form was dissolved in a 1:4 mixed liquid (150 mL) of n-heptane and ethyl acetate, and then a 4 N hydrogen chloride/ethyl acetate solution (30 mL) was slowly added at 0 to 5° C. with stirring to obtain a suspension.

The resulting solid was collected by filtration to obtain the title compound (33 g) as a hydrochloride.

The obtained hydrochloride of the title compound was desalted with a 4 N aqueous sodium hydroxide solution (20 mL) to obtain the title compound (29.2 g, yield: 88%).

$^1$H-NMR (400 MHz, CDCl$_3$): δ7.10-7.35 (m, 7H), 6.97 (d, 1H, J=8 Hz), 6.77 (d, 1H, J=8 Hz), 6.67 (d, 2H, J=8 Hz), 3.70 (d, 1H, J=13 Hz), 3.68 (s, 3H), 3.55 (d, 1H, J=13 Hz), 2.90-3.20 (m, 6H), 2.60-2.70 (m, 1H), 2.46 (dd, 1H, J=4, 12 Hz), 2.29 (d, 2H, J=6 Hz), 1.99 (dt, 1H, J=3, 13 Hz), 1.75 (dt, 1H, J=5, 13 Hz), 1.50-1.65 (m, 3H), 1.30 (s, 9H), 1.20-1.35 (m, 1H), 1.10-1.20 (m, 1H), 1.00-1.10 (m, 2H), 0.70-0.85 (m, 2H), 0.40-0.50 (m, 2H), 0.00-0.15 (m, 2H).

Example 2

Synthesis of (1S,3aR,5aS,6R,11bS,11cS)-3-benzyl-14-(cyclopropylmethyl)-10-methoxy-11-(3-methoxyphenoxy)-2,3,3a,4,5,6,7,11c-octahydro-1H-6,11b-(epiminoethano)-1,5a-methanonaphtho[1,2-e]indole

[Chemical Formula 14]

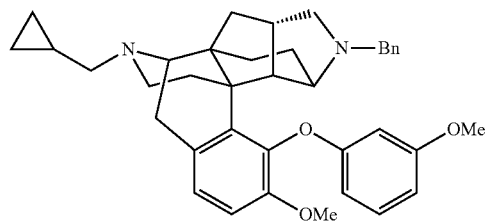

By a similar method to that in Example 1, using 3-bromoanisole as a halobenzene, the title compound (0.12 g, yield: 99%) was obtained.

$^1$H-NMR (400 MHz, CDCl$_3$): δ7.15-7.30 (m, 5H), 7.11 (t, 1H, J=8 Hz), 6.97 (d, 1H, J=8 Hz), 6.78 (d, 1H, J=8 Hz), 6.52 (dd, 1H, J=2, 8 Hz), 6.38 (t, 1H, J=2 Hz), 6.32 (dd, 1H, J=2, 8 Hz), 3.75 (s, 3H), 3.72 (d, 1H, J=13 Hz), 3.68 (s, 3H), 3.58 (d, 1H, J=13 Hz), 2.90-3.25 (m, 6H), 2.60-2.75 (m, 3H), 2.47 (dd, 1H, J=4, 12 Hz), 2.29 (d, 2H, J=6 Hz), 1.99 (dt, 1H, J=3, 13 Hz), 1.76 (dt, 1H, J=5, 13 Hz), 1.50-1.70 (m, 2H), 1.10-1.20 (m, 1H), 1.00-1.10 (m, 2H), 0.70-0.85 (m, 2H), 0.40-0.50 (m, 2H), 0.00-0.15 (m, 2H).

Example 3

Synthesis of (1S,3aR,5aS,6R,11bS,11cS)-3-benzyl-14-(cyclopropylmethyl)-10-methoxy-11-(p-toluyloxy)-2,3,3a,4,5,6,7,11c-octahydro-1H-6,11b-(epiminoethano)-1,5a-methanonaphtho[1,2-e]indole

[Chemical Formula 15]

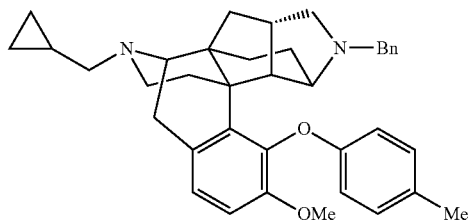

By a similar method to that in Example 1, using 4-bromotoluene as a halobenzene, the title compound (0.11 g, yield: 90%) was obtained.

¹H-NMR (400 MHz, CDCl₃): δ7.15-7.30 (m, 5H), 7.02 (d, 2H, J=8 Hz), 6.97 (d, 1H, J=8 Hz), 6.77 (d, 1H, J=8 Hz), 6.65 (d, 2H, J=8 Hz), 3.73 (d, 1H, J=13 Hz), 3.67 (s, 3H), 3.59 (d, 1H, J=13 Hz), 2.90-3.25 (m, 6H), 2.60-2.75 (m, 3H), 2.47 (dd, 1H, J=4, 12 Hz), 2.35 (d, 2H, J=6 Hz), 2.29 (s, 3H), 1.99 (dt, 1H, J=3, 13 Hz), 1.76 (dt, 1H, J=5, 13 Hz), 1.50-1.70 (m, 2H), 1.10-1.20 (m, 1H), 1.00-1.10 (m, 2H), 0.70-0.85 (m, 2H), 0.40-0.50 (m, 2H), 0.00-0.15 (m, 2H).

Comparative Example 1

Synthesis of ethyl 3-(((1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole-11-yl)oxy)benzoate

[Chemical Formula 16]

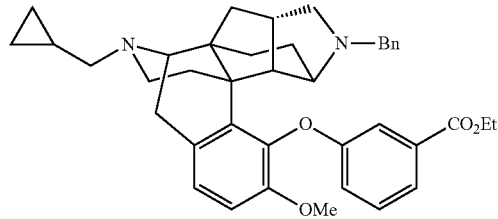

By a similar method to that in Example 1, using ethyl 3-iodobenzoate as a halobenzene, the title compound (0.19 g, yield: 73%) was obtained.

¹H-NMR (400 MHz, CDCl₃): δ7.65 (d, 1H, J=8 Hz), 7.48 (s, 1H), 7.15-7.35 (m, 6H), 7.00 (d, 1H, J=8 Hz), 6.91 (dd, 1H, J=3, 8 Hz), 6.78 (d, 1H, J=8 Hz), 4.46 (q, 2H, J=7 Hz), 3.71 (d, 1H, J=13 Hz), 3.65 (s, 3H), 3.57 (d, 1H, J=13 Hz), 2.90-3.20 (m, 6H), 2.60-2.80 (m, 2H), 2.46 (dd, 1H, J=4, 12 Hz), 2.29 (d, 2H, J=6 Hz), 2.00 (dt, 1H, J=3, 13 Hz), 1.76 (dt, 1H, J=5, 13 Hz), 1.50-1.70 (m, 3H), 1.38 (t, 3H, J=7 Hz), 1.10-1.25 (m, 1H), 1.00-1.10 (m, 2H), 0.70-0.85 (m, 2H), 0.40-0.50 (m, 2H), 0.00-0.15 (m, 2H).

Comparative Example 2

Synthesis of 3-(((1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole-11-yl)oxy)benzonitrile

[Chemical Formula 17]

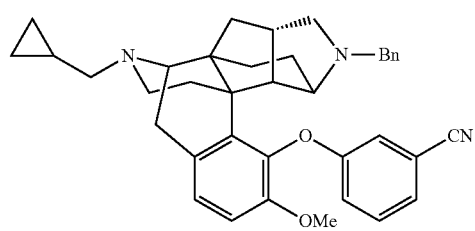

By a similar method to that in Example 1, using 3-bromobenzonitrile as a halobenzene, the title compound (0.05 g, yield: 44%) was obtained.

¹H-NMR (400 MHz, CDCl₃): δ7.15-7.40 (m, 7H), 6.90-7.05 (m, 3H), 6.78 (d, 1H, J=8 Hz), 3.71 (d, 1H, J=13 Hz), 3.67 (s, 3H), 3.58 (d, 1H, J=13 Hz), 2.95-3.15 (m, 6H), 2.65-2.80 (m, 2H), 2.48 (dd, 1H, J=4, 12 Hz), 2.25-2.35 (m, 2H), 2.00 (dt, 1H, J=3, 13 Hz), 1.76 (dt, 1H, J=5, 13 Hz), 1.50-1.70 (m, 3H), 1.15-1.30 (m, 1H), 1.00-1.05 (m, 1H), 0.85-0.95 (m, 1H), 0.65-0.85 (m, 2H), 0.40-0.55 (m, 2H), 0.00-0.15 (m, 2H).

Comparative Example 3

Synthesis of 4-(((1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole-11-yl)oxy)benzonitrile

[Chemical Formula 18]

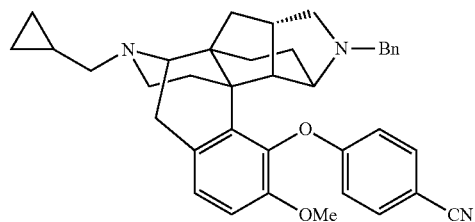

By a similar method to that in Example 1, using 4-bromobenzonitrile as a halobenzene, the title compound (0.085 g, yield: 75%) was obtained.

¹H-NMR (400 MHz, CDCl₃): δ7.52 (d, 2H, J=8 Hz), 7.15-7.30 (m, 5H), 7.02 (d, 1H, J=8 Hz), 6.81 (d, 2H, J=8 Hz), 6.77 (d, 1H, J=8 Hz), 3.70 (d, 1H, J=13 Hz), 3.66 (s, 3H), 3.56 (d, 1H, J=13 Hz), 2.90-3.15 (m, 6H), 2.70-2.80 (m, 1H), 2.60-2.70 (m, 1H), 2.47 (dd, 1H, J=4, 12 Hz), 2.20-2.35 (m, 2H), 1.95 (dt, 1H, J=3, 13 Hz), 1.76 (dt, 1H, J=5, 13 Hz), 1.50-1.70 (m, 3H), 1.15-1.30 (m, 1H), 1.00-1.10 (m, 1H), 0.90-0.95 (m, 1H), 0.65-0.85 (m, 2H), 0.40-0.55 (m, 2H), 0.00-0.15 (m, 2H).

Comparative Example 4

Synthesis of (1S,3aR,5aS,6R,11bS,11cS)-3-benzyl-14-(cyclopropylmethyl)-10-methoxy-11-(pyridine-3-yloxy)-2,3,3a,4,5,6,7,11c-octahydro-1H-6,11b-(epiminoethano)-1,5a-methanonaphtho[1,2-e]indole

[Chemical Formula 19]

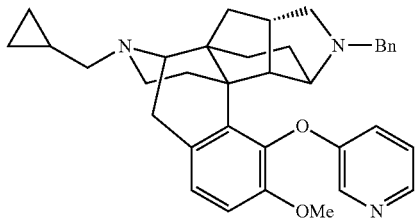

By a similar method to that in Example 1, using 3-iodopyridine as a halogenated heteroaryl, the title compound (0.14 g, yield: 80%) was obtained.

$^1$H-NMR (400 MHz, CDCl$_3$): δ8.15-8.25 (m, 2H), 7.15-7.35 (m, 6H), 7.02 (d, 2H, J=8 Hz), 6.78 (d, 1H, J=8 Hz), 3.72 (d, 1H, J=13 Hz), 3.67 (s, 3H), 3.56 (d, 1H, J=13 Hz), 2.95-3.15 (m, 6H), 2.65-2.80 (m, 2H), 2.47 (dd, 1H, J=4, 12 Hz), 2.29 (d, 2H, J=6 Hz), 2.00 (dt, 1H, J=3, 13 Hz), 1.76 (dt, 1H, J=5, 13 Hz), 1.55-1.70 (m, 2H), 1.15-1.30 (m, 2H), 1.00-1.10 (m, 1H), 0.90-1.00 (m, 1H), 0.70-0.85 (m, 2H), 0.45-0.55 (m, 2H), 0.00-0.15 (m, 2H).

Comparative Example 5

Synthesis of (1S,3aR,5aS,6R,11bS,11cS)-3-benzyl-14-(cyclopropylmethyl)-10-methoxy-11-(thiophene-3-yloxy)-2,3,3a,4,5,6,7,11c-octahydro-1H-6,11b-(epiminoethano)-1,5a-methanonaphtho[1,2-e]indole

[Chemical Formula 20]

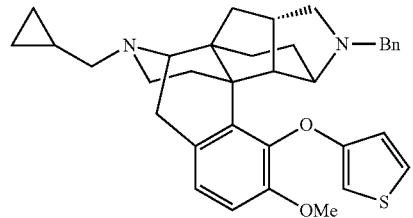

By a similar method to that in Example 1, using 3-bromothiophene as a halogenated heteroaryl, the title compound (0.081 g, yield: 71%) was obtained.

$^1$H-NMR (400 MHz, CDCl$_3$): δ7.10-7.40 (m, 6H), 6.96 (d, 1H, J=8 Hz), 6.70-6.80 (m, 2H), 6.05 (dd, 1H, J=2, 3 Hz), 3.72 (s, 3H), 3.70 (d, 1H, J=13 Hz), 3.57 (d, 1H, J=13 Hz), 2.90-3.20 (m, 6H), 2.60-2.80 (m, 2H), 2.40-2.50 (m, 1H), 2.28 (d, 2H, J=6 Hz), 1.90-2.00 (m, 1H), 1.70-1.75 (m, 1H), 1.50-1.70 (m, 3H), 1.00-1.20 (m, 3H), 0.65-0.85 (m, 2H), 0.40-0.50 (m, 2H), 0.00-0.15 (m, 2H).

2. Production of ((1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole) in which the Diaryl Ether Derivative Produced in 1 Above is Used as a Starting Material

Example 4

Synthesis of (1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole dihydrochloride

[Chemical Formula 21]

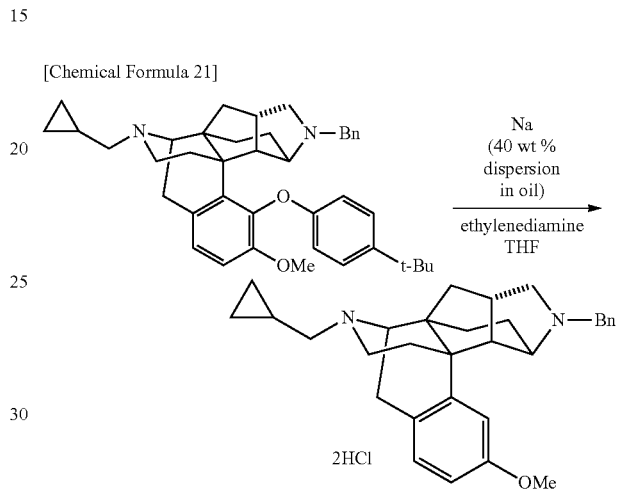

In a 200 mL round bottom flask, tetrahydrofuran (25 mL) was dissolved in ethylenediamine (25 mL) under a nitrogen atmosphere. Under an ice bath, metal sodium (5 g, 40 wt % dispersion in oil purchased from Alfa Aesar) was added to the obtained solution. After stirring for 10 minutes, into the obtained reaction liquid, a tetrahydrofuran (25 mL) solution of (1S,3aR,5aS,6R,11bS,11cS)-3-benzyl-11-(4-(tert-butyl)phenoxy)-14-(cyclopropylmethyl)-10-methoxy-2,3,3a,4,5,6,7,11c-octahydro-1H-6,11b-(epiminoethano)-1,5a-methanonaphtho[1,2-e]indole (5 g, 1 equivalent) obtained in the Example 1 was added dropwise with stirring. After 1 hour, the reaction was analyzed by MS and thin layer chromatography to confirm that the raw material remains. The reaction liquid was heated to room temperature. After 1 hour, the reaction was analyzed by MS and thin layer chromatography, and the disappearance of the raw material was confirmed.

Ethanol (25 mL) was added dropwise to the reaction liquid while stirring the reaction liquid in an ice bath, and a mixed liquid (25 mL) of ethanol/water=4/1 was further added. Finally, water (25 mL) was added dropwise, and the resulting mixture was stirred for 1 hour to obtain a reaction liquid 1.

1 mL of the reaction liquid 1 was fractionated, and the production amounts of the target product and the by-product were checked by HPLC.

The remaining reaction liquid 1 was concentrated under reduced pressure, and a 6 N HCl aqueous solution was added to the obtained residue in an ice bath to adjust the pH of the liquid solution to 2. The obtained reaction liquid was washed with heptane (100 mL×3 times), and the pH of the aqueous layer was adjusted to 12 with a 4 N NaOH aqueous solution. This aqueous layer was extracted with ethyl acetate (200 mL×3 times). The combined organic layers were dried over anhydrous sodium sulfate, the anhydrous sodium sulfate was filtered off, and then the combined organic layers were concentrated under reduced pressure to obtain a title compound crude product.

The obtained crude product was dissolved in a mixed solvent of ethyl acetate/heptane=1/4 (25 mL), and a 4 N hydrogen chloride/ethyl acetate solution (5 mL) was slowly added at 0 to 5° C. with stirring to obtain a suspension.

The resulting solid was collected by filtration to obtain the title compound (4.18 g, 96%, purity: 94%).

The yield (%) of the target product obtained and the content (%) of the by-product corresponding to (b-1) are shown in Table 1. The production amounts of the target product ((1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole) and the by-product ((1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole-11-ol) (hereinafter, referred to as a by-product A) in the reaction mixture were determined as an area percentage (%) of HPLC.

No by-product A was observed, and the yield of the target product was as high as 94%. This result shows that the dephenylation reaction was not observed, and the dephenoxylation reaction highly selectively occurred.

$^1$H-NMR (400 MHz, DMSO-$d_6$): δ10.40-10.65 (m, 1H), 9.29 (brs, 1H), 7.70-7.80 (m, 1H), 7.60-7.70 (m, 1H), 7.40-7.55 (m, 3H), 7.18 (d, 0.5H, J=8 Hz), 7.13 (d, 0.5H, J=8 Hz), 6.70-6.90 (m, 2H), 4.20-4.40 (m, 2H), 4.00-4.10 (m, 2H), 3.73 (s, 1.5H), 3.72 (s, 1.5H), 2.85-4.00 (m, 11H), 1.80-2.10 (m, 2H), 1.30-1.75 (m, 4H), 1.00-1.25 (m, 2H), 0.50-0.75 (m, 3H), 0.30-0.45 (m, 1H).

Reference Example 2

Using the diaryl ether derivative produced in Reference Example 1 as a starting material, a dephenoxylation reaction was performed under Na-Benkeser reaction conditions by a method in accordance with Example 4 to produce the target product ((1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole). The yield (%) of the target product obtained and the content (%) of the by-product A are shown in Table 1.

The by-product A was produced by 5%, and the yield of the target product was 79%. This result shows that the dephenoxylation reaction was dominant, but the dephenylation reaction also occurred.

Example 5

Using the diaryl ether derivative produced in Example 2 as a starting material, a dephenoxylation reaction was performed under Na-Benkeser reaction conditions by a method in accordance with Example 4 to produce the target product ((1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole). The yield (%) of the target product obtained and the content (%) of the by-product A are shown in Table 1.

The by-product A was produced by 1%, and the yield of the target product was as high as 89%. This result shows that though the dephenylation reaction slightly occurred, the dephenoxylation reaction occurred more selectively than in Reference Example 2.

Example 6

Using the diaryl ether derivative produced in Example 3 as a starting material, a dephenoxylation reaction was performed under Na-Benkeser reaction conditions by a method in accordance with Example 4 to produce the target product ((1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole). The yield (%) of the target product obtained and the content (%) of the by-product A are shown in Table 1.

No by-product A was observed, and the yield of the target product was as high as 93%. This result shows that the dephenylation reaction was not observed, and the dephenoxylation reaction highly selectively occurred.

Comparative Example 6

Using the diaryl ether derivative produced in Comparative Example 1 as a starting material, a dephenoxylation reaction was performed under Na-Benkeser reaction conditions by a method in accordance with Example 4 to produce the target product ((1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole). The yield (%) of the target product obtained and the content (%) of the by-product A are shown in Table 1.

The by-product A was produced by 3%, and the yield of the target product was 30%. This result shows that the dephenoxylation reaction was dominant, but the dephenylation reaction also occurred, and the selectivity of the dephenoxylation reaction was reduced as compared with Reference Example 2.

Comparative Example 7

Using the diaryl ether derivative produced in Comparative Example 2 as a starting material, a dephenoxylation reaction was performed under Na-Benkeser reaction conditions by a method in accordance with Example 4 to produce the target product ((1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole). The yield (%) of the target product obtained and the content (%) of the by-product A are shown in Table 1.

The by-product A was produced by 6%, and the yield of the target product was 42%. This result shows that the dephenoxylation reaction was dominant, but the dephenylation reaction also occurred, and the selectivity of the dephenoxylation reaction was reduced as compared with Reference Example 2.

Comparative Example 8

Using the diaryl ether derivative produced in Comparative Example 3 as a starting material, a dephenoxylation reaction was performed under Na-Benkeser reaction conditions by a method in accordance with Example 4 to produce the target product ((1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole). The yield (%) of the target product obtained and the content (%) of the by-product A are shown in Table 1.

The by-product A was produced by 35%, and the yield of the target product was 2%. This result shows that the dephenylation reaction occurred more dominantly than the dephenoxylation reaction.

Comparative Example 9

Using the diaryl ether derivative produced in Comparative Example 4 as a starting material, a dephenoxylation reaction was performed under Na-Benkeser reaction conditions by a method in accordance with Example 4 to produce the target product ((1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole). The yield (%) of the target product obtained and the content (%) of the by-product A are shown in Table 1.

The by-product A was produced by 10%, and the yield of the target product was 76%. This result shows that the dephenoxylation reaction was dominant, but the dephenylation reaction also occurred, and the selectivity of the dephenoxylation reaction was reduced as compared with Reference Example 2.

Comparative Example 10

Using the diaryl ether derivative produced in Comparative Example 5 as a starting material, a dephenoxylation reaction was performed under Na-Benkeser reaction conditions by a method in accordance with Example 4 to produce the target product ((1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole). The yield (%) of the target product obtained and the content (%) of the by-product A are shown in Table 1.

The by-product A was produced by 3%, and the yield of the target product was 67%. This result shows that the dephenoxylation reaction was dominant, but the dephenylation reaction also occurred, and the yield of the dephenoxylation reaction was lower than that of Reference Example 2.

The test results of Reference Example 2, Examples 4 to 6, and Comparative Examples 6 to 10 described above are shown in Table 1 below.

TABLE 1

| Test | Starting material | By-product A (%) | Target product (%) |
|---|---|---|---|
| Reference Example 2 | | 5 | 79 |
| Example 4 | | none | 94 |
| Example 5 | | 1 | 89 |
| Example 6 | | none | 93 |

TABLE 1-continued

| Test | Starting material | By-product A (%) | Target product (%) |
|---|---|---|---|
| Comparative Example 6 | (structure with -O-phenyl-CO₂Et, OMe) | 3 | 30 |
| Comparative Example 7 | (structure with -O-phenyl-CN (meta), OMe) | 6 | 42 |
| Comparative Example 8 | (structure with -O-phenyl-CN (para), OMe) | 35 | 2 |
| Comparative Example 9 | (structure with -O-pyridin-3-yl, OMe) | 10 | 76 |
| Comparative Example 10 | (structure with -O-thiophen-3-yl, OMe) | 3 | 67 |

INDUSTRIAL APPLICABILITY

According to the present invention, a method for highly selectively producing a morphinan derivative from a diaryl ether derivative by suppressing production of a phenol form as a by-product, the method being applicable to an industrial production method can be provided.

The invention claimed is:

1. A method for producing a morphinan derivative represented by Formula (II) below:

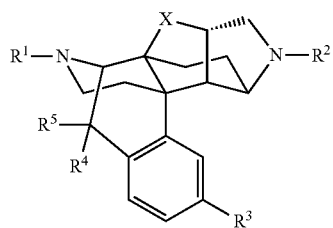

wherein $R^1$ represents a hydrogen atom, a $C_{1-10}$ alkyl group optionally having a substituent, a $C_{3-6}$ cycloalkyl group optionally having a substituent, a $C_{2-6}$ alkenyl group optionally having a substituent, a $C_{6-10}$ aryl group optionally having a substituent, or a heteroaryl group optionally having a substituent, $R^2$ represents an amino protecting group, $R^3$ represents a methoxy group, $R^4$ and $R^5$ are same or different and represent a hydrogen atom or a hydroxy group, and X represents O or $CH_2$, said method comprising:

allowing metal sodium and ethylenediamine to act on a morphinan derivative represented by Formula (I) below:

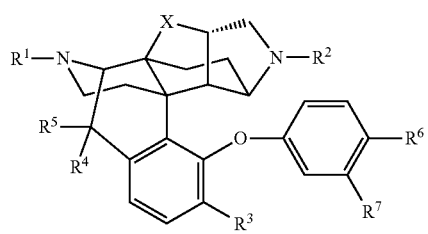

wherein $R^1$ to $R^5$ and X have a meaning same as above, $R^6$ and $R^7$ are same or different and represent a hydrogen atom or an electron-donating group, wherein $R^6$ and $R^7$ are not simultaneously a hydrogen atom, and in presence of an auxiliary solvent.

2. The method for producing a morphinan derivative according to claim 1, wherein $R^1$ is a hydrogen atom.

3. The method for producing a morphinan derivative according to claim 1, wherein $R^1$ is a $C_{1-10}$ alkyl group substituted with a $C_{3-6}$ cycloalkyl group optionally having a substituent.

4. The method for producing a morphinan derivative according to claim 1, wherein $R^1$ is a cyclopropylmethyl group.

5. The method for producing a morphinan derivative according to claim 1, wherein $R^2$ is a benzyl group.

6. The method for producing a morphinan derivative according to claim 1, wherein $R^3$ is a $C_{1-10}$ alkoxy group.

7. The method for producing a morphinan derivative according to claim 1, wherein $R^3$ is a methoxy group.

8. The method for producing a morphinan derivative according to claim 1, wherein $R^4$ and $R^5$ are a hydrogen atom.

9. The method for producing a morphinan derivative according to claim 1, wherein $R^6$ is a $C_{1-10}$ alkyl group, $OR^8$ ($R^8$ represents a hydrogen atom or a $C_{1-10}$ alkyl group optionally having a substituent), or $NR^9R^{10}$ ($R^9$ and $R^{10}$ are same or different and represent a hydrogen atom or a $C_{1-10}$ alkyl group optionally having a substituent).

10. The method for producing a morphinan derivative according to claim 1, wherein $R^6$ is a $C_{1-10}$ alkyl group optionally having a substituent.

11. The method for producing a morphinan derivative according to claim 1, wherein $R^6$ is a tert-butyl group.

12. The method for producing a morphinan derivative according to claim 1, wherein $R^6$ is a hydrogen atom.

13. The method for producing a morphinan derivative according to claim 1, wherein $R^7$ is a hydrogen atom.

14. The method for producing a morphinan derivative according to claim 1, wherein $R^7$ is a $C_{1-10}$ alkyl group optionally having a substituent, $OR^{11}$ ($R^{11}$ represents a hydrogen atom or a $C_{1-10}$ alkyl group optionally having a substituent), or $NR^{12}R^{13}$ ($R^{12}$ and $R^{13}$ are same or different and represent a hydrogen atom or a $C_{1-10}$ alkyl group optionally having a substituent).

15. The method for producing a morphinan derivative according to claim 1, wherein $R^7$ is a $C_{1-10}$ alkoxy group optionally having a substituent.

16. The method for producing a morphinan derivative according to claim 1, wherein $R^7$ is a methoxy group.

17. The method for producing a morphinan derivative according to claim 1, wherein the metal sodium is used in an amount of 1 to 10 equivalents relative to the morphinan derivative of the Formula (I).

18. The method for producing a morphinan derivative according to claim 1, wherein the metal sodium is a metal sodium dispersion.

19. The method for producing a morphinan derivative according to claim 1, wherein the auxiliary solvent is an aromatic hydrocarbon solvent or an ether solvent.

20. The method for producing a morphinan derivative according to claim 1, wherein a reaction temperature is −30° C. to 150° C.

21. The method for producing a morphinan derivative according to claim 1, wherein a reaction temperature is 0° C. to 30° C.

22. A morphinan derivative represented by Formula (I) below:

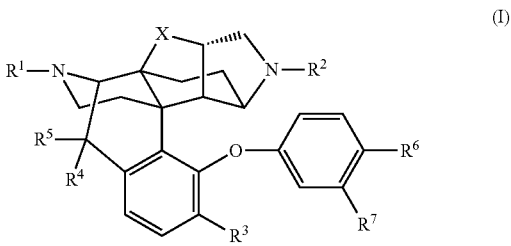

wherein R¹ represents a hydrogen atom, a $C_{1-10}$ alkyl group optionally having a substituent, a $C_{3-6}$ cycloalkyl group optionally having a substituent, a $C_{2-6}$ alkenyl group optionally having a substituent, a $C_{6-10}$ aryl group optionally having a substituent, or a heteroaryl group optionally having a substituent, R² represents an amino protecting group, R³ represents a methoxy group, R⁴ and R⁵ are same or different and represent a hydrogen atom or a hydroxy group, R⁶ and R⁷ are same or different and represent a hydrogen atom or an electron-donating group, wherein R⁶ and R⁷ are not simultaneously a hydrogen atom, and X represents O or $CH_2$.

23. The morphinan derivative according to claim 22, wherein R¹ is a hydrogen atom.

24. The morphinan derivative according to claim 22, wherein R¹ is a $C_{1-10}$ alkyl group substituted with a $C_{3-6}$ cycloalkyl group optionally having a substituent.

25. The morphinan derivative according to claim 22, wherein R¹ is a cyclopropylmethyl group.

26. The morphinan derivative according to claim 22, wherein R² is a benzyl group.

27. The morphinan derivative according to claim 22, wherein R³ is a $C_{1-10}$ alkoxy group.

28. The morphinan derivative according to claim 22, wherein R³ is a methoxy group.

29. The morphinan derivative according to claim 22, wherein R⁴ and R⁵ are a hydrogen atom.

30. The morphinan derivative according to claim 22, wherein R⁶ is a $C_{1-10}$ alkyl group, OR⁸ (R⁸ represents a hydrogen atom or a $C_{1-10}$ alkyl group optionally having a substituent), or NR⁹R¹⁰ (R⁹ and R₁₀ are same or different and represent a hydrogen atom or a $C_{1-10}$ alkyl group optionally having a substituent).

31. The morphinan derivative according to claim 22, wherein R⁶ is a $C_{1-10}$ alkyl group optionally having a substituent.

32. The morphinan derivative according to claim 22, wherein R⁶ is a tert-butyl group.

33. The morphinan derivative according to claim 22, wherein R⁶ is a hydrogen atom.

34. The morphinan derivative according to claim 22, wherein R⁷ is a hydrogen atom.

35. The morphinan derivative according to claim 22, wherein R⁷ is a $C_{1-10}$ alkyl group optionally having a substituent, $OR_{11}$ ($R^{11}$ represents a hydrogen atom or a $C_{1-10}$ alkyl group optionally having a substituent), or $NR^{12}R^{13}$ ($R^{12}$ and $R^{13}$ are same or different and represent a hydrogen atom or a $C_{1-10}$ alkyl group optionally having a substituent).

36. The morphinan derivative according to claim 22, wherein R⁷ is a $C_{1-10}$ alkoxy group optionally having a substituent.

37. The morphinan derivative according to claim 22, wherein R⁷ is a methoxy group.

38. A morphinan derivative selected from (1S,3aR,5aS,6R,11bS,11cS)-3-benzyl-11-(4-(tert-butyl)phenoxy)-14-(cyclopropylmethyl)-10-methoxy-2,3,3a,4,5,6,7,11c-octahydro-1H-6,11b-(epiminoethano)-1,5a-methanonaphtho[1,2-e]indole, (1S,3aR,5aS,6R,11bS,11cS)-3-benzyl-14-(cyclopropylmethyl)-10-methoxy-11-(3-methoxyphenoxy)-2,3,3a,4,5,6,7,11c-octahydro-1H-6,11b-(epiminoethano)-1,5a-methanonaphtho[1,2-e]indole, and (1S,3aR,5aS,6R,11bS,11cS)-3-benzyl-14-(cyclopropylmethyl)-10-methoxy-11-(p-toluyloxy)-2,3,3a,4,5,6,7,11c-octahydro-1H-6,11b-(epiminoethano)-1,5a-methanonaphtho[1,2-e]indole.

\* \* \* \* \*